United States Patent
Hishinuma et al.

(10) Patent No.: US 11,116,856 B2
(45) Date of Patent: Sep. 14, 2021

(54) HAND DRYER WITH UV DISINFECTION DEVICE

(71) Applicant: BLV Licht- und Vakuumtechnik GmbH, Steinhoering (DE)

(72) Inventors: Nobuyuki Hishinuma, Steinhoering (DE); Yasuhiko Wakahata, Steinhoering (DE)

(73) Assignee: BLV LICHT- UND VAKUUMTECHNIK GMBH, Steinhoering (DE)

( * ) Notice: Subject to any disclaimer, the term of this patent is extended or adjusted under 35 U.S.C. 154(b) by 14 days.

(21) Appl. No.: 16/161,828

(22) Filed: Oct. 16, 2018

(65) Prior Publication Data
US 2019/0117802 A1    Apr. 25, 2019

(30) Foreign Application Priority Data

Oct. 17, 2017    (DE) .................. 10 2017 009 637.6

(51) Int. Cl.
*A61L 2/00*    (2006.01)
*A61L 2/26*    (2006.01)
(Continued)

(52) U.S. Cl.
CPC ............ *A61L 2/0047* (2013.01); *A47K 10/48* (2013.01); *A61L 2/0076* (2013.01); *A61L 2/10* (2013.01);
(Continued)

(58) Field of Classification Search
None
See application file for complete search history.

(56) References Cited

U.S. PATENT DOCUMENTS 5,459,944 A * 10/1995 Tatsutani ............... A47K 10/48
                                                        34/202
5,498,394 A *  3/1996 Matschke .............. A47K 10/48
                                                      250/455.11
(Continued)

FOREIGN PATENT DOCUMENTS

DE    102012008253    10/2013
EP        1866627     9/2013
(Continued)

OTHER PUBLICATIONS

Buonanno et al., "Germicidal Efficacy and Mammalian Skin Safety of 222-nm UV Light", Radiation Research 187,493-501 (2017).*
(Continued)

*Primary Examiner* — Luan V Van
(74) *Attorney, Agent, or Firm* — Grossman, Tucker, Perreault & Pfleger, PLLC

(57) ABSTRACT

A hand dryer with a housing in which a cavity accessible from outside through a housing opening is formed for accommodating hands to be dried by means of an airflow, and with a device for generating the airflow, as well as a device for generating UV radiation comprising at least one lamp that emits light in the ultraviolet wavelength range, which is arranged in the housing in such a manner that it emits UV radiation into the cavity. The device for generating UV radiation is designed in such a manner that the UV radiation emitted into the cavity with a wavelength in the range from 228 to 380 nm has a maximum intensity of 20% of the intensity of the UV radiation emitted into the cavity with a wavelength in the range from 200 to 380 nm.

14 Claims, 6 Drawing Sheets

(51) Int. Cl.
  *B01J 21/06* (2006.01)
  *B01J 35/00* (2006.01)
  *A47K 10/48* (2006.01)
  *A61L 2/10* (2006.01)

(52) U.S. Cl.
  CPC .............. *A61L 2/26* (2013.01); *B01J 21/063* (2013.01); *B01J 35/004* (2013.01); *A61L 2202/11* (2013.01)

(56) References Cited

U.S. PATENT DOCUMENTS

2013/0283629 A1   10/2013  Bueker
2018/0078101 A1*   3/2018  Satermo .................. A47K 10/48
2018/0214585 A1*   8/2018  Piper ....................... C02F 1/325

FOREIGN PATENT DOCUMENTS

| EP | 2842870 | | 3/2015 |
| JP | 2005-305031 | | 11/2005 |
| JP | 2006-238940 | | 9/2006 |
| KR | 20110042990 | * | 4/2011 |
| WO | 2007/015040 | | 2/2007 |
| WO | 2013/175202 | | 11/2013 |
| WO | 2016/114650 | | 7/2016 |
| WO | 2016/156861 | | 10/2016 |

OTHER PUBLICATIONS

Wikipedia, "Ultraviolet germicidal irradiation", Feb. 20, 2019. https://en.wikipedia.org/wiki/Ultraviolet_germicidal_irradiation.

* cited by examiner

HAND DRYER WITH UV DISINFECTION DEVICE

FIELD

The invention relates to a hand dryer, in particular a hand dryer in which hands inserted through a housing opening can be dried in a cavity by means of an airflow.

BACKGROUND

Such hand dryers are generally known in the prior art. They usually comprise a fan or blower with which air is blown through one or more nozzles onto the hands inserted into the cavity and thus drying the hands. WO 2007/015040 A1, for example, describes a hand dryer in which an airflow in the form of a thin air curtain is blown at a high velocity from slot-shaped nozzles onto the hands. The liquid blown off the hands is captured in a collecting area. The air used for drying, however, is partially recirculated inside the hand dryer and partially reaches the area surrounding the hand dryer. Yet this way contaminations adhering to the hands, in particular germs such as spores or bacteria, can be carried along by the air and get into the ambient air.

In many areas, the accumulation of contaminations and in particular germs in the air is not desired or even allowed. Reference can be made in this connection, e.g., to hospitals or nursing homes, production sites with stricter demands for clean ambient conditions, e.g. in the production of pharmaceuticals or food, or in gastronomy. Independently of these specific areas, demands for good hygienic conditions have generally become stricter.

Besides keeping the surrounding area clean, in some areas a disinfection or even sterilization of the hands and, if necessary, of the arms of people working in these areas is required. After normal hand washing, about 5% of the germs located on the hands prior to hand washing still remain on the skin. Additional measures are thus required in order to reduce this number of germs. These measures usually consist in washing with germicidal substances such as alcohol-based liquids or gel-like compositions. A complete disinfection or sterilization, however, requires a very thorough washing, which is time-consuming. In many cases, the required thoroughness is found lacking, which results in an infection risk by germs remaining on hands and arms.

In order to reduce the germs during hand drying, DE 102012008253 A1 and EP 2656762 A2 have already proposed a hand dryer comprising various means for germ reduction, inter alia in the form of a lamp emitting UV radiation. More specific details are not revealed in the application. However, research preceding this invention has shown that only the use of certain UV lamps and a certain arrangement of the same will lead to the desired germ reduction without endangering the health of the user.

SUMMARY

Accordingly, the object of the invention is to indicate a hand dryer that reduces the number of germs on the hands of the user and in the airflow recirculated and/or reaching the surrounding area during the drying process without jeopardizing the health of the user.

This object is achieved with the hand dryer according to claim 1. Preferred embodiments are indicated in the dependent claims.

In its broadest aspect, the invention thus relates to a hand dryer with a housing in which a cavity accessible from outside through a housing opening is configured to accommodate hands to be dried by means of an airflow, with a device for generating said airflow, as well as with a device for generating UV radiation comprising at least one lamp that emits radiation in the ultraviolet wavelength range and that is arranged in the housing in such a way that it emits UV radiation into the cavity. The device for generating UV radiation is designed in such a manner that the UV radiation that is emitted into the cavity with a wavelength in the range from 228 to 380 nm has a maximum intensity of 20% of the intensity of the UV radiation emitted into the cavity with a wavelength in the range from 200 to 380 nm.

The hand dryer according to the invention uses a device for generating UV radiation that emits a specific spectrum of the radiation into the cavity. The radiation spectrum is optimized so that the UV radiation reaching the cavity in a wavelength range from 200 to 380 nm is overwhelmingly predominantly, i.e. at least 80%, in the wavelength range below 228 nm. Merely a maximum of 20% of the intensity of the UV radiation emitted into the cavity (which here always means the radiation in the range from 200 to 380 nm) is in the wavelength range from 228 to 380 nm. The intensity of the UV radiation in the latter range preferably accounts for a maximum of 15%, more preferably a maximum of 10%, and especially a maximum of 7%, of the intensity of the UV radiation (200 to 380 nm) emitted into the cavity.

The UV spectrum with an increased proportion of radiation in the wavelength range below 228 nm and a reduced intensity in the range from 228 to 380 nm as implemented in the hand dryer according to the invention results in an almost complete extermination of the germs located on the skin, in particular an almost complete elimination of bacteria, including multi-resistant bacteria. Moreover, the UV radiation emitted into the cavity is not absorbed by human DNA or RNA so that it does not have a mutagenic effect on human cells. Ocular damage also does not occur in this wavelength range. This would not be the case, however, if the entire spectrum of the UV radiation were emitted into the cavity. Particularly in the wavelength range above 250 nm, UV radiation is absorbed by both human RNA and DNA and can lead to strand breaks and subsequent formation of double bonds or dimers. Numerous human proteins also absorb UV radiation in the higher UV-C wavelength range and can, like the human eye, be damaged by it. The device for generating UV radiation used in accordance with the invention thus selectively emits UV radiation in the low UV-C range while specifically keeping a sufficient distance from the critical wavelength range above 250 nm, so that the intensity of the UV radiation in the wavelength range from 228 to 380 nm amounts to a maximum of 20% of the total UV radiation in the wavelength range from 200 to 380 nm. This way, the health risks for the user of the hand dryer according to the invention can be reduced to a minimum, while germs and in particular bacteria are practically completely exterminated. This applies not only to germs located on the hands of the user but also to germs carried along with the airflow inside the hand dryer.

According to the invention, the radiation spectrum described above can be achieved in various manners. A first possibility is to choose a lamp that has a main emission wavelength below 228 nm. It is preferred here to use a lamp which inherently and without further intervention already provides the UV radiation intensity distribution according to the invention. Lamps that are particularly suitable for this purpose include dielectric barrier discharge lamps and in particular KrCl and KrBr excimer barrier discharge lamps. The main wavelengths of these two excimer barrier discharge lamps are 222 nm and 207 nm, respectively. Both lamp types only emit a minimum amount of ultraviolet radiation above 228 nm. These two excimer barrier discharge lamps thus represent particularly suitable examples for use in the hand dryer according to the invention.

A second possibility for the generation of the desired UV spectrum consists in the use of a lamp that generates radiation which excites a fluorescent material, which in turn exhibits radiation with a main wavelength below 228 nm. Such lamps, in which the originally generated radiation is converted into radiation of another wavelength using a fluorescent material, are generally known. According to the invention, noble gas barrier discharge lamps are preferably used for generating the excitation radiation. Particularly suitable types include xenon, krypton and argon barrier discharge lamps. Materials that can be employed as the fluorescent material (UV-C emitting luminescent material) include, e.g., lanthanum phosphate praseodymium, $LaPO_4$:Pr.

Another possibility for the generation of the desired UV spectrum consists in using at least one lamp that generates UV radiation in a wavelength range that is broader than the desired wavelength range and filtering out the undesired wavelength ranges by means of a filter material. Such filter materials are also generally known. It is preferred to use filters that filter out UV radiation with a wavelength in the range from 228 to 300 nm and preferably from 230 to 260 nm. The filtering out of UV radiation with approximately 254 nm is particularly important, as this wavelength can damage numerous human proteins as well as human RNA and DNA.

The possibilities for generating the desired UV spectrum described above can be implemented either individually or in any combination. In particular, it is possible, for example, to use the lamp types specifically selected on the basis of their emission spectrum in the first and second variants in combination with a suitable filter. This way, it is possible to realize a particularly small proportion of UV radiation in the wavelength range from 228 to 380 nm.

The filter material can be arranged in the device for generating UV radiation in any suitable manner. One possibility consists in applying the filter material as a coating to the lamp bulb or incorporating the same in the material of the lamp bulb. Suitable filter materials can contain hafnium oxide and/or silicon oxide. A filter material that contains alternating layers of hafnium oxide and silicon oxide is preferred.

The at least one lamp of the device for generating UV radiation can be arranged inside the hand dryer in various manners. In a preferred variant, the lamp bulb of the lamp is arranged inside the housing in such a manner that a part of the same projects into the cavity while a predominant part of the lamp bulb is located outside the cavity. Unlike the variant in which the lamp is arranged behind a light emission window that sits flush with the wall delimiting the cavity, the UV radiation can reach the entire cavity better and generally free it from germs. However, most of the lamp bulb is still arranged outside the cavity and is thus well protected against damage and contamination by dirty water. In the context of the invention, "most of the lamp bulb" is to be understood as a volume occupied by the lamp bulb that accounts for more than 50% of the total volume of the lamp bulb. Preferably, not more than 30% of the lamp bulb volume should project into the cavity.

In another variant, the at least one lamp is located completely inside the cavity with the entire lamp bulb. This possibility is in particular an option when the cavity is large enough to accommodate the at least one lamp and still leave enough room for the hands of the user. In this variant, it is advantageous to use lamps comprising a tubular lamp bulb with a small diameter.

In principle, a single UV lamp in the hand dryer can be sufficient in accordance with the invention. Preferably, however, at least two lamps are arranged on opposite sides of the cavity and irradiate the hands of the user with UV radiation from two sides. If the at least one lamp has a tubular lamp bulb, it is preferably arranged essentially parallel to the plane of the housing opening. "Essentially parallel" here means a maximum inclination of 15° with respect to the plane of the opening. The inclination is preferably not greater than 5° and in particular not greater than 2° relative to the plane of the opening. Alternatively, it is also possible to use lamps with an essentially spherical or ovoid lamp bulb. It is also possible to arrange multiple lamps next to one another on each side of the cavity. With respect to their inclination relative to the plane of the housing opening, the above statements regarding tubular lamp bulbs apply here accordingly.

In a preferred embodiment of the invention, the part of the lamp bulb located inside the cavity is separated from the cavity of the hand dryer by a window component. The window component acts as a protection for the lamp and preferably seals the cavity from the space in which the lamp is arranged in an air- and moisture-tight manner. If more than one lamp is used, each of them can be individually protected by a window component or a single window component can be used for multiple lamps. If a filter material for filtering out undesired UV wavelength ranges is used, it can be provided, for example, as a coating on the window component. Alternatively, it is possible to manufacture the window component partially or entirely from a filter material. It is of course also possible to use filter materials on or in both the lamp bulb and the window component. In addition, the filter material can also be used to filter out other wavelength ranges outside the ultraviolet range. As regards suitable materials, reference can be made to the above description.

In order to ensure that a maximum proportion of the radiation generated by the device for generating UV radiation enters the cavity of the hand dryer, it is preferred to surround the lamb bulb with a reflector which leaves free a radiation emission opening, said reflector reflecting the UV radiation with a wavelength below 228 nm towards the cavity. Depending on the type of the lamp used, it is of course also possible for the reflector to reflect radiation with other wavelengths, separating, if necessary, undesired UV radiation by means of a filter material. In principle, any suitable reflector known from the prior art can be implemented as the reflector. The reflector can be, e.g., a metal coating of the lamp bulb. Alternatively, a metal sleeve that is arranged on the exterior of the lamp bulb and that leaves free the radiation emission opening is also an option. In the case of dielectric barrier discharge lamps, the metal sleeve can simultaneously be used as the outer electrode of the lamp. The reflector not only provides for an effective emission of the UV radiation into the cavity but also prevents UV radiation from reaching the interior of the housing and damaging the components arranged there if the lamp is partially located outside the cavity. This way, the service life of the hand dryer can be extended.

It has proven expedient to configure the radiation emission opening in such a way that radiation is emitted towards the cavity at an opening angle of at least 30°. This ensures a sufficiently large irradiation area and thus an essentially complete irradiation of the user's hands when inserted into the cavity.

In principle, the basic structure of the hand dryer according to the invention can correspond to that of conventional hand dryers and differ from the latter with regard to the device for generating UV radiation only. According to the invention, hand dryers are preferably used that in their basic structure correspond to the hand dryers described in DE 102012008253 A1, EP 2656762 A2 and WO 2007/015040 A1. This concerns in particular the supply of air to the drying cavity. The invention thus also uses flat nozzles for this purpose, which blow thin air curtains at a high velocity onto the hands to be dried, preferably at a velocity of at least 15 m/s. A hand dryer according to the invention thus expediently has, arranged opposite each another on the longitudinal sides of the housing opening, two flat nozzles with which the airflow is blown into the cavity. An inclination angle of the nozzle openings in relation to the plane of the housing opening of at least 7° has proven particularly preferable here. This way, the air blown into the cavity is guided obliquely and at a relatively small angle onto and along the hands to be dried. As the device for generating the airflow, a blower or fan can be used in a manner known per se.

With respect to the flat nozzle with which air is blown into the cavity, the at least one lamp is expediently arranged in such a manner that it is arranged opposite the flat nozzle within a strip-shaped area located on a sidewall delimiting the cavity. The upper and lower edges of the strip-shaped area correspond to section lines with which the boundaries of an angular range intersect the sidewall, the angular range being based on the direction of the air exiting the flat nozzle as the center plane and extending at plus and minus 45° on both sides of the center plane. With respect to the flat nozzle, the lamp is thus oriented on the opposite side of the cavity in such a manner that the moisture blown off the user's hands and the germs contained therein are blown towards the lamp and are thus exposed to the UV radiation with great reliability.

The guidance of the airflow inside the hand dryer can generally also be implemented in a known manner. In one variant, the air supplied to the cavity is not recirculated and escapes from the cavity into the area surrounding the hand dryer. In another variant, at least a part of the air blown into the cavity for drying the hands is recirculated and refed to the cavity. For this purpose, the hand dryer according to the invention in this case has at least one exhaust air duct and at least one air supply duct, which communicate with the cavity in such a manner that the airflow can be circulated through the exhaust air and air supply ducts and the cavity. In principle, the device for generating the airflow—such as a blower or fan—can be arranged at any position within this ventilation circuit, i.e. in the exhaust air duct, the air supply duct or in the area of the cavity. The device for generating the airflow is preferably arranged in the area of the exhaust air duct through which the airflow is guided out of the cavity.

In order to prevent germs from escaping from the area of the hand dryer into its surroundings to the greatest extent possible, it can be advantageous to provide the hand dryer according to the invention with a design that is as closed as possible (see DE 102012008253 A1 and EP 2656762 A2). On the other hand, there are other known hand dryers, such as the one described in WO 2007/015040 A1, that have a relatively open design, the purpose of which is to avoid dynamic pressure and to allow air to flow off quickly. For this reason, for example, the cavity for drying the hands is configured to be open to the sides. In principle, both of these designs can be employed in the context of the invention.

Irrespective of the design of the hand dryer, a further improvement in terms of a germ reduction can be achieved according to the invention by providing at least areas of at least a section of the walls delimiting the cavity with a photocatalyst. The latter is a compound capable of breaking down organic compounds under the influence of radiation. More specifically, in the present case, a photocatalyst is used which, when exposed to the radiation generated by the device for generating UV radiation, contributes to the elimination of germs in the cavity. This is achieved, for example, by means of the release of ozone and/or radicals—such as OH radicals formed from water—by the photocatalyst under the influence of UV radiation, which react with the germs and destroy them. A preferred photocatalyst is titanium dioxide, which is, e.g., contained in a coating applied to the surface of the walls surrounding the cavity or incorporated in the material of the walls. In order to eliminate germs on the walls of the cavity to the greatest extent possible, the walls are provided or coated, as far as possible, completely with the photocatalyst.

BRIEF DESCRIPTION OF THE DRAWINGS

The invention is explained in greater detail below with the help of the drawings. In the purely schematic drawings, identical parts are designated by identical reference numbers. The figures show:

FIG. 4b is an alternative lamp arrangement in a view corresponding to that of FIG. 4a;

DETAILED DESCRIPTION

Figure 1:
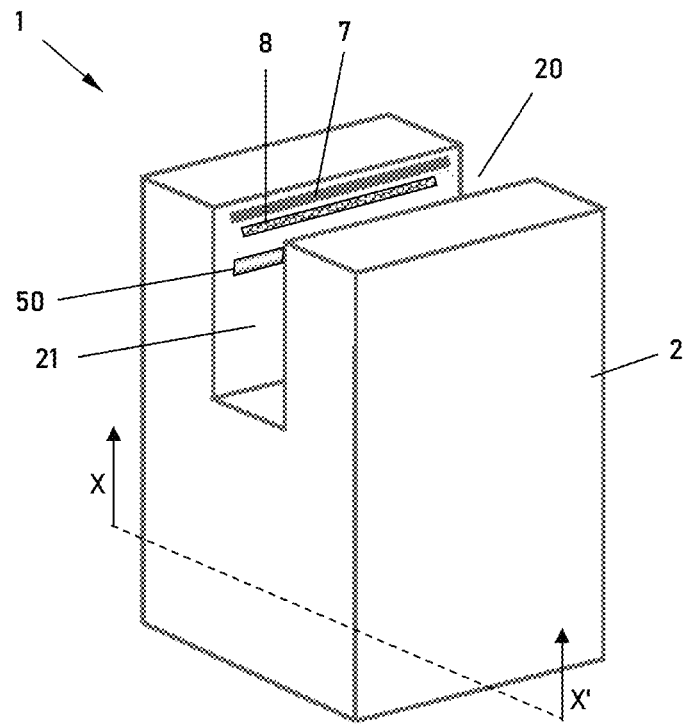
FIG. 1 is an embodiment of a hand dryer according to the invention.
Figure 3:
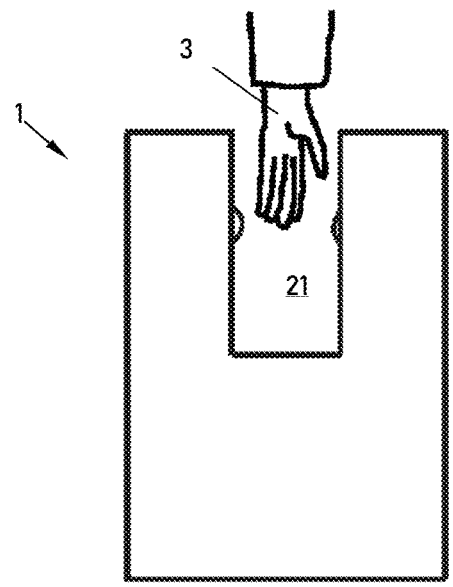
FIG. 3 is a side view of the hand dryer according to FIG. 1 during use by a user.

FIG. 1 shows a very simplified perspective representation of a hand dryer 1 according to the invention with a housing 2 that has on its top side a housing opening 20 extending through the entire housing width, said opening connecting to a cavity 21 that, like the housing opening 20, extends across the entire housing width. The cavity 21 is large enough for a user to insert his hands 3 completely into the cavity 21 through the housing opening 20. This is suggested in the side view of the hand dryer in FIG. 3, which depicts a part of an arm as well as a hand 3 of the user partially inserted into the cavity 21.

Figure 2:
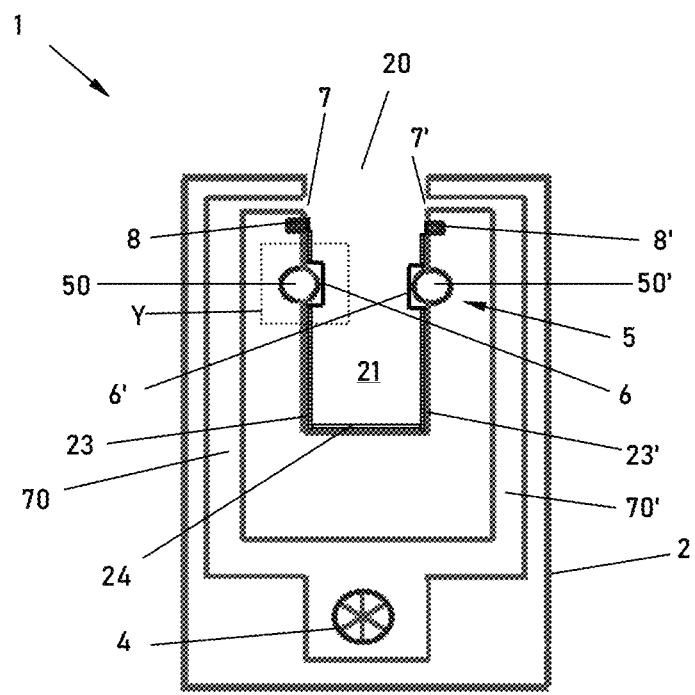
FIG. 2 is the cross section of the hand dryer according to FIG. 1 along line X-X.

The cross-sectional view of FIG. 2 shows that the lower area of the housing 2 contains a cavity in which a fan 4 is arranged that conveys air at a high velocity through two ventilation ducts 70, 70' towards two flat nozzles 7, 7', which are adjacent to the housing opening 20 and which open into the cavity 21 on opposite sides. At a velocity of at least 15 m/s, air is blown out of the flat nozzles 7, 7' towards the user's hands 3 inserted into the cavity 21. The fan 4 is not activated until the two sensors 8, 8' detect an object—usually the hands of a user—in the gap between them. The fan 4 is then operated for a predetermined period of time. In addition, the two lamps 50, 50', which are part of a device 5 for generating UV radiation, are also switched on. The device 5 emits UV radiation into the cavity with a wavelength in the range from 200 to 380 nm, of which a maximum of 20% of the intensity is in a wavelength range from 228 to 380 nm.

Figure 2A:
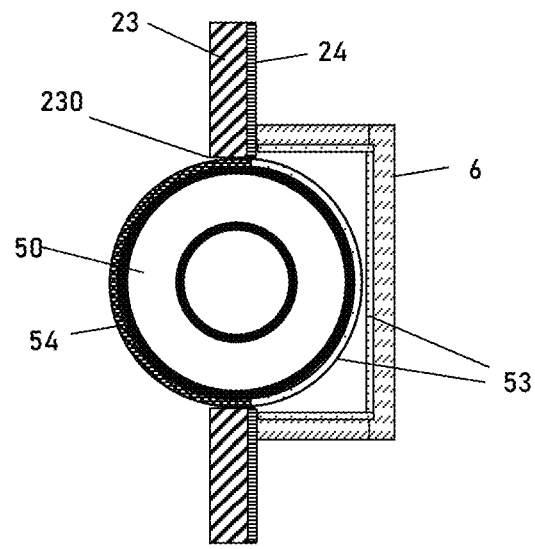
FIG. 2a is a detailed enlargement of the area Y in FIG. 2.

FIG. 2a shows an enlarged representation of part Y of the device 5 for generating UV radiation. The lamp arrangement on the opposite side of the cavity 21 is configured accordingly. The lamp 50 in the example shown is a krypton halide excimer barrier discharge lamp, more specifically a KrCl or KrBr excimer barrier discharge lamp, with a tubular lamp bulb. Said bulb is arranged so as to extend parallel to the plane of the housing opening 20 and simultaneously parallel to the sensor 8 and to the discharge opening of the flat nozzle 7, which are arranged between the lamp bulb and the housing opening 20. The flat nozzle in this specific case is 25 cm long. The lamb bulb 51 is arranged inside a slot-shaped opening 230, which is also 25 cm long, in a sidewall 23 delimiting the cavity 21, in such a manner that about one third of the volume occupied by the lamp bulb is inside the cavity 21, while the remaining approximately two thirds of the lamp bulb is located outside the cavity 21. The partial insertion of the lamp bulb 51 into the cavity 21 ensures that the radiation emitted by the lamp can reach all areas of the cavity 21 without excessively reducing the space available for the hands of the user or subjecting the lamp to an excessive risk of damage and contamination. The protection of the lamp is additionally ensured by a window component 6, which completely covers the part of the lamp bulb 51 projecting into the cavity 21 and seals the slot-shaped opening 230 vis-à-vis the cavity 21 in an air- and moisture-tight manner.

Figure 4A:
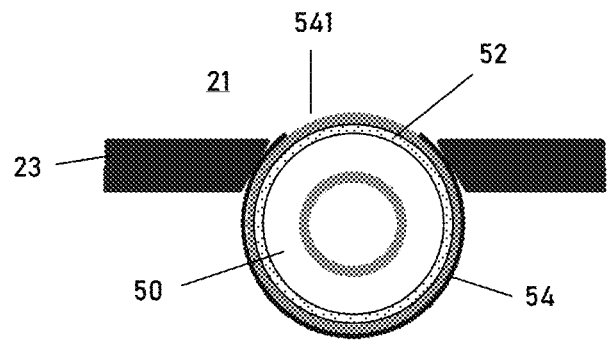
FIG. 4a is the arrangement of a lamp in relation to the cavity and to a sidewall delimiting the cavity in a cross-section perpendicular to the longitudinal axis of the lamp.
Figure 4B:
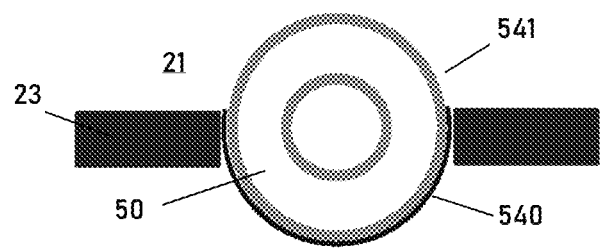

The area of the lamp bulb 51 that does not project into the cavity 21 is surrounded by a reflector 54, which in this case has the shape of a slotted metal sleeve 540, while the slot opening 541 forms a radiation emission opening towards the cavity 21 (see also FIGS. 4a and 4b). Alternatively, the reflector 54 can also be a metal coating. If a metal sleeve 540 is used, it can simultaneously act as the outer electrode of the dielectric barrier discharge lamp. In the example shown in FIG. 2, the part of the lamp bulb 51 projecting into the cavity 21 is coated with a filter material 53 that is capable of filtering UV radiation with wavelengths in the range above 228 nm out of the radiation emitted into the cavity. Alternatively or additionally, filter material 53 can also be applied to the window component 6 as a coating or the window component 6 can be manufactured overall from a filter material.

Figure 2B:
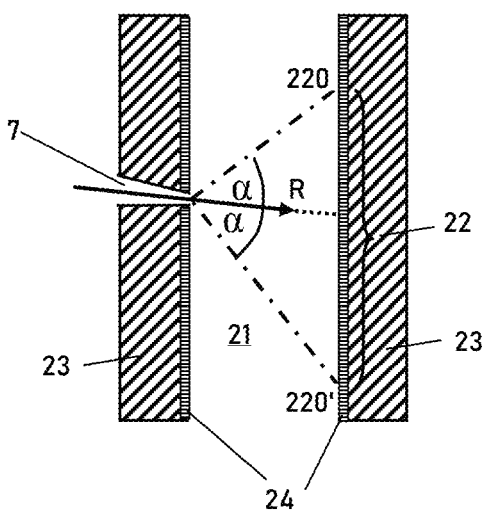
FIG. 2b is the arrangement of a lamp in relation to a flat nozzle in the hand dryer according to FIGS. 1 and 2.

FIG. 2b schematically illustrates the arrangement of the lamp 50' in relation to the opposite flat nozzle 7. The same applies to the corresponding lamp 50 and the opposite flat nozzle 7'. As is evident from this figure, the flat nozzle 7 has a slight inclination towards the interior of the cavity 21. The air enters the cavity 21 at a velocity of at least 15 m/s as an air curtain along the flow direction R illustrated by the arrow and ensuing dashed line. Viewed across the entire width of the flat nozzle 7, the flow direction, which in the cross-section is depicted as a line, constitutes a plane, on the basis of which an angular range $\alpha$ is defined in accordance with the invention, the angular range opening up towards the opposite side wall 23' in the shape of a wedge. The section formed by the wedge-shaped region on the sidewall 23' constitutes a strip-shaped area 22 with a transverse extension and with an upper edge 220 and a lower edge 220'. According to the invention, the lamp 50' is arranged within this strip-shaped area, while the angle $\alpha$ is 90° and splits into equal parts on both sides of the flow direction plane R, i.e. respectively into $\alpha/2=45°$ above and below the plane R.

As is further evident from FIGS. 2, 2a and 2b, the walls 23 delimiting the cavity and the cavity floor are provided with a coating 24. This coating contains a photocatalyst, specifically titanium dioxide. When exposed to UV radiation, the photocatalyst causes the formation of radicals, e.g. OH radicals from water, and ozone, each of which have a germicidal effect. This way, the accumulation of germs on the cavity walls is prevented.

FIGS. 4a and 4b show two different possibilities for the arrangement of the lamp bulb 51 in relation to the sidewall 23 and the cavity 21. While the lamp bulb 51 projects into the cavity 21 only very slightly in FIG. 4a, in FIG. 4b approximately 40% of the volume of the lamp bulb 51 is located inside the cavity 21. The further the lamp bulb projects into the cavity 21, the better the latter can be irradiated with UV radiation, although the risk of damage and contamination increases and the lamp bulb and the window component 6 covering the same take up more space inside the cavity. In addition, FIG. 4a shows another example of a lamp 50, namely of the kind in which a coating of fluorescent material 52 such as $LaPO_4$:Pr converts the generated radiation into the UV radiation emitted into the cavity 21 with the increased proportion of radiation with wavelengths below 228 nm. This can be, e.g., a noble gas barrier discharge lamp.

Figure 5:
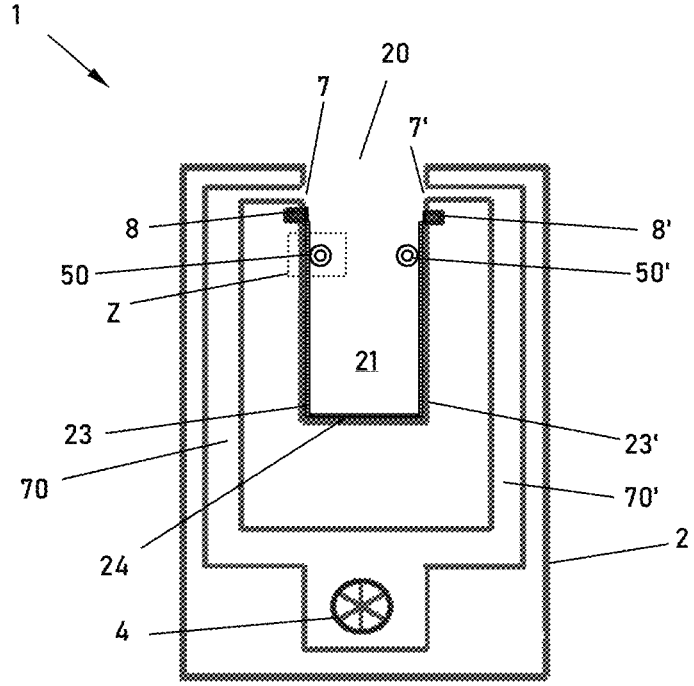
FIG. 5 is an alternative embodiment of the hand dryer according to FIG. 1 in a cross-section along line X-X.

FIG. 5 shows an alternative embodiment of a hand dryer 1 according to the invention. It essentially differs from the hand dryer shown in FIG. 2 by the arrangement of the lamps 50, 50'. These are now located completely inside the cavity 21. The tubular lamp bulbs, which extend essentially parallel to the opening 20, expediently have a diameter that is as small as possible, e.g. 15 mm, in order to leave as much space as possible in the cavity 21 for the hands of the user.

Figure 5A:
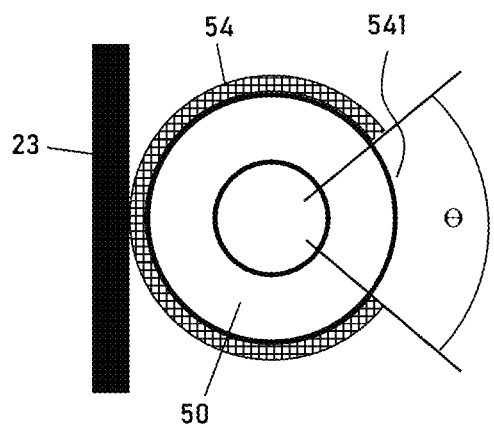
FIGS. 5a-c are various lamp arrangements in the area of section Z shown in FIG. 5.
Figure 5B:
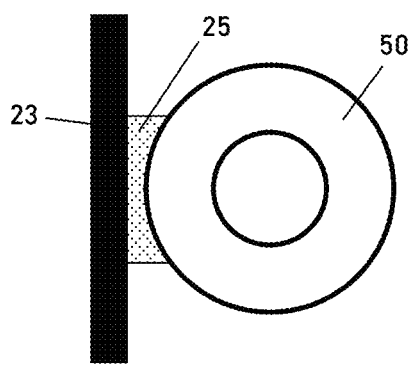
Figure 5C:
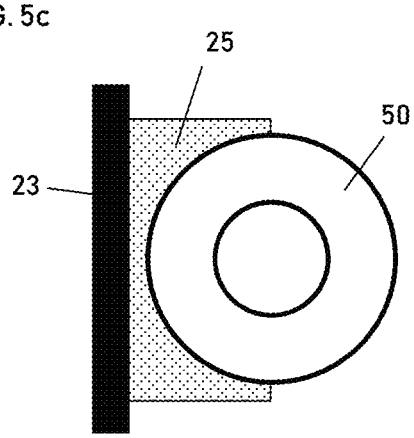

FIGS. 5a to 5c show, in an enlargement of the area Z shown in FIG. 5, various possibilities for the arrangement of the lamp 50. In FIG. 5a, the lamp bulb of the lamp 50 is surrounded by a reflector 54, which leaves open a radiation emission opening 541 towards the cavity 21. This opening allows UV radiation to exit into the cavity 21 at an opening angle $\theta$ of more than 30°, in this specific case at approximately 80°. The opening angle is selected depending on the dimensions of the hand dryer 1 and so that a sufficient irradiation of the cavity and, as far as possible, a complete irradiation of the hands of a user can occur.

FIGS. 5b and 5c show alternative lamp arrangements in which the lamp 50 is fixed to a sidewall 23 of the cavity 21 by means of a fixing component 25. The opening angle $\theta$ here is determined via the size of the fixing component 25. In the case shown in FIG. 5b, the fixing component covers only about 60° of the circumference of the lamp bulb, which results in an opening angle of about 300°. In the case shown in FIG. 5c, the fixing component covers about half the circumference of the lamp bulb, resulting in an opening angle of about 180°.

Research was conducted regarding the comparative effectiveness of the invention in relation to a conventional hand drying method. In the example of the invention, a hand dryer with the structure illustrated in FIGS. 1 and 2 was used, KrCl excimer barrier discharge lamps with a main wavelength of 222 nm respectively being used as the lamps 50, 50'. These lamps were respectively operated at about 20 W, while the irradiation intensity on the hand surface was about 3 mW/cm$^2$. The total dose of the UV radiation at 222 nm during a drying time of approximately 5 seconds was on average 15 mJ/cm$^2$. Upon completion of the drying time, a sample was taken from the subject's hands with Petrifilm commercially available from 3M and incubated in accordance with the manufacturer's instructions. Afterwards, the colonies found on the respective Petrifilm plate were counted. Two samples were taken for each test series. The result of the test series was derived from the average count. The experiments comprised the following test series:

1) The hands were washed thoroughly with soap and dried in the hand dryer without emission of UV radiation into the cavity 21.
2) The hands were washed thoroughly with soap and dried in the hand dryer with emission of UV radiation into the cavity 21.
3) The hands were not washed and were dried in the hand dryer without emission of UV radiation into the cavity 21.
4) The hands were not washed and were dried in the hand dryer with emission of UV radiation into the cavity 21.

Figure 6A:
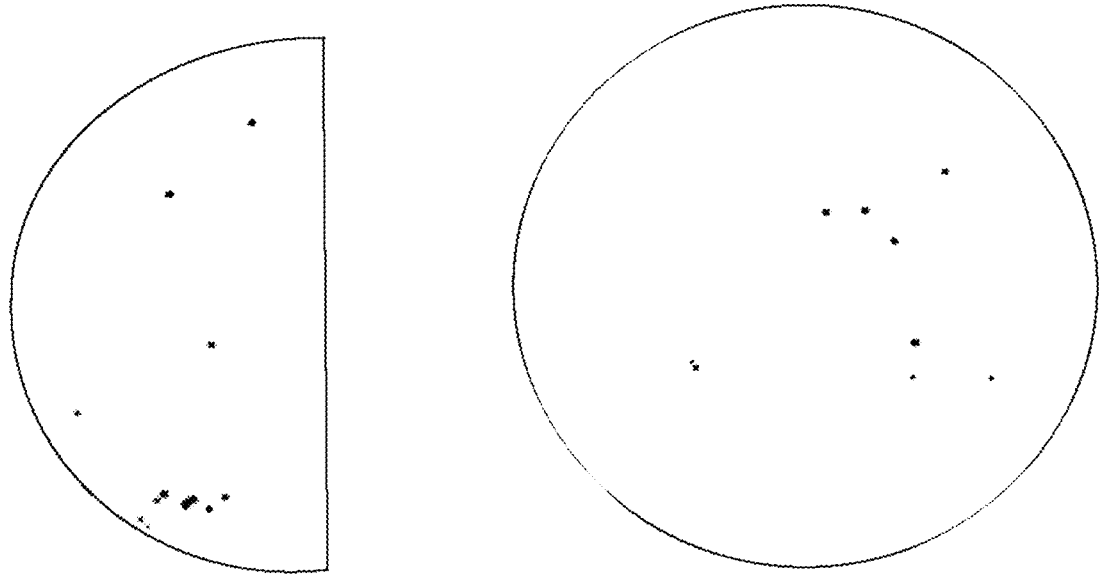
FIGS. 6a-d are top views of Petri dishes in which samples were cultivated that were taken from the hand of a subject after different washing and sterilization techniques.
Figure 6B:
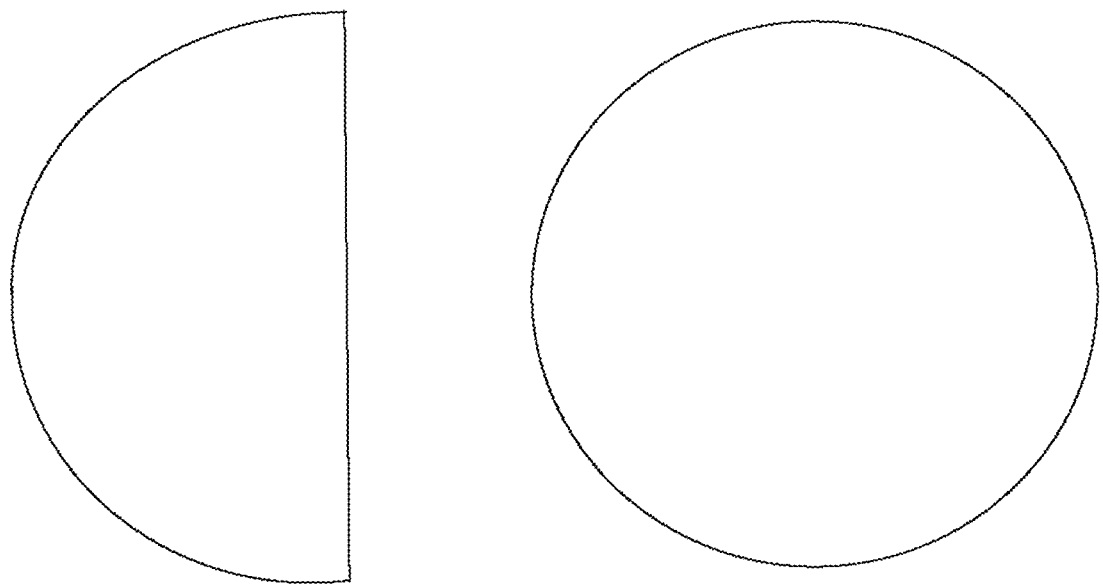
Figure 6C:
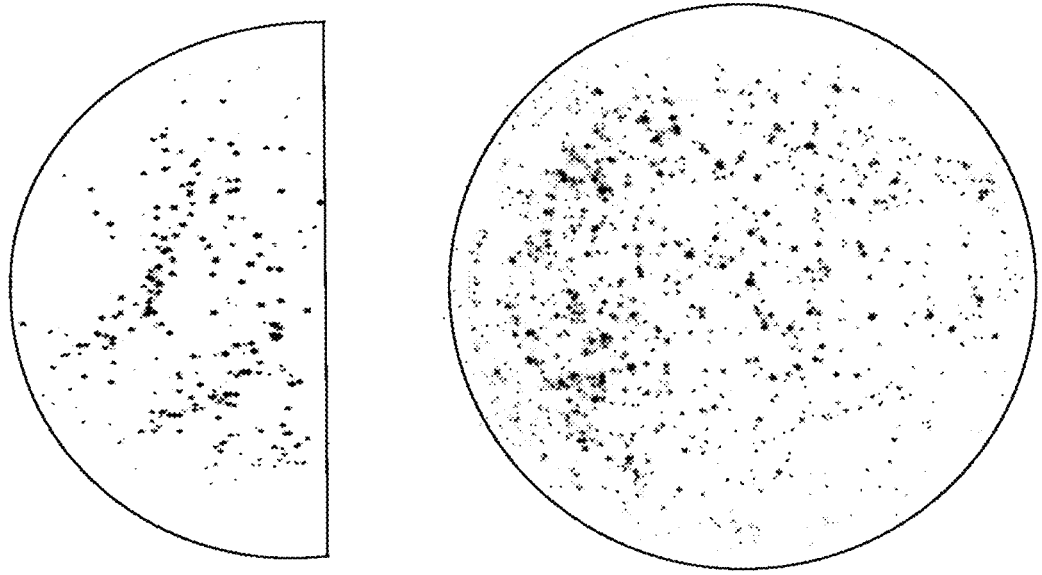
Figure 6D:
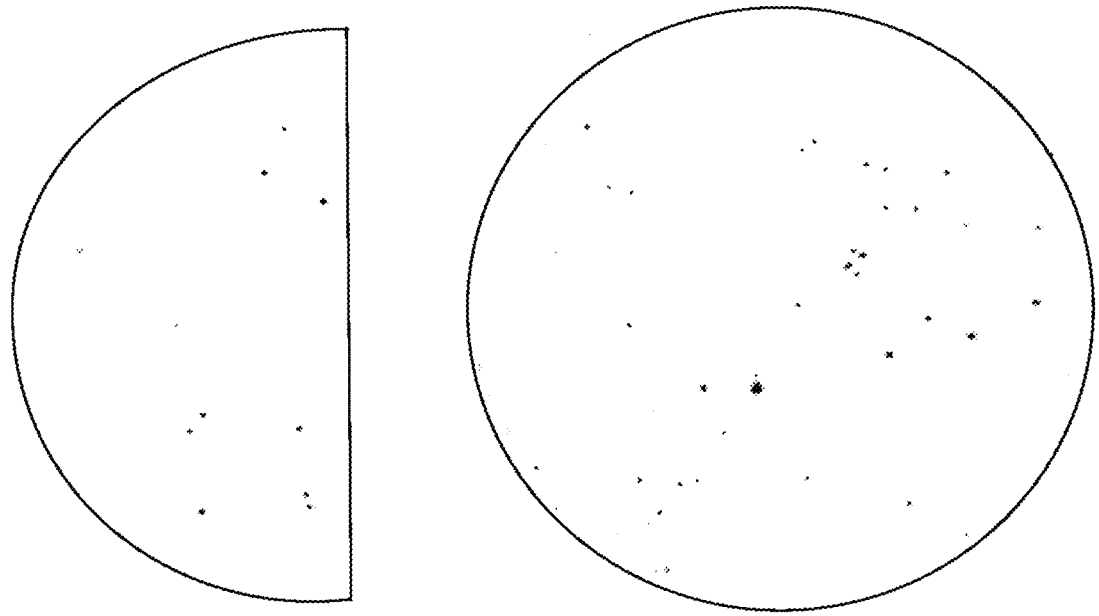

Photographs of the two samples taken from the palms for each test series 1 to 4 are shown in FIGS. 6a to 6d, although only half of the Petrifilm plate is shown in the left section of the images. FIG. 6a shows the result of the two samples from test series 1, for which the count of the colonies on the Petrifilm plates yielded 24 and 13 colonies, respectively, and thus an average of 18.5 colonies. FIG. 6b shows the Petrifilm plates of test series 2 with two colonies and one colony, respectively, and thus an average of 1.5 colonies. Test series 3 resulted in 480 and 812 colonies, respectively, and thus an average of 646 colonies, on the Petrifilm plates shown in FIG. 6c. Finally, test series 4 resulted in 32 and 43 colonies, respectively, and thus an average of 37.5 colonies, on the Petrifilm plates depicted in FIG. 6d.

The above results show that a relatively effective cleaning of the hands is in principle already possible with thorough hand washing and drying, corresponding to a residual germ rate of about 3%, compared to test series 3 in which the hands were merely dried and there was no germ reduction. Test series 4 illustrates that a significant reduction of the germs located on the hands, namely a germ rate of approximately 5 to 8% compared to test series 3, can already be achieved even in the case of unwashed hands as a result of the mere exposure to UV radiation. The best results by far, namely practically completely germ-free hands with a residual germ rate of about 0.2% compared to test series 3, were achieved in test series 2, i.e. by thorough washing of the hands followed by drying in the hand dryer in accordance with the invention with emission of the UV radiation wavelength range selected in accordance with the invention.

What is claimed is:

1. A hand dryer comprising:
    a housing in which a cavity accessible from outside through a housing opening is formed for accommodating hands to be dried by an airflow;
    a device for generating the airflow;
    a device for generating UV radiation comprising at least one lamp that emits light in an ultraviolet wavelength range, which is arranged in the housing in such a manner that the device for generating UV radiation emits an UV radiation into the cavity;
    wherein the device for generating UV radiation is configured such that the UV radiation emitted into the cavity has a wavelength in a range from 200 nm to 380 nm, wherein the UV radiation includes a maximum of 20% having a wavelength in a range of 228 nm to 380 nm; and
    wherein a lamp bulb of the at least one lamp is arranged in the housing such that a part of the lamp bulb projects into the cavity while a predominant part of the lamp bulb is located outside the cavity.

2. The hand dryer according to claim 1, wherein the device for generating UV radiation is configured such that the UV radiation emitted into the cavity having the wavelength in the range from 200 nm to 380 nm includes a maximum of 15% having the wavelength in the range of 228 nm to 380 nm.

3. The hand dryer according to claim 1, wherein the at least one lamp comprises at least one of the following:
    the at least one lamp has a main emission wavelength below 228 nm; and/or
    the at least one lamp generates radiation which excites a fluorescent material, the radiation emitted by excitation of the fluorescent material having a main wavelength below 228 nm; and/or
    the at least one lamp in combination with a filter material that filters out UV radiation with the wavelength in the range from 228 nm to 300 nm.

4. The hand dryer according to claim 3, wherein the filter material is attached to a lamp bulb of the at least one lamp and/or a window component, or the window component comprises the filter material.

5. The hand dryer according to claim 1, wherein a lamp bulb of the at least one lamp is arranged completely inside the cavity.

6. The hand dryer according to claim 1, wherein the part of the lamp bulb located inside the cavity is separated from the cavity by a window component.

7. The hand dryer according to claim 1, wherein a lamp bulb of the at least one lamp is surrounded by a reflector, the reflector leaving open a radiation emission opening and reflecting the UV radiation with the wavelength below 228 nm towards the cavity.

8. The hand dryer according to claim 7, wherein the reflector is a metal coating of the lamp bulb or a metal sleeve, which metal sleeve is arranged on an exterior of the lamp bulb and which leaves free the radiation emission opening.

9. The hand dryer according to claim 7, wherein the radiation emission opening is configured to allow the UV radiation to pass towards the cavity at an opening angle ($\Theta$) of at least 30°.

10. The hand dryer according to claim 1, wherein the at least one lamp further comprises two lamps, which are arranged on opposite sides of the cavity.

11. The hand dryer according to claim 1, wherein at least one flat nozzle on respective opposite sides of the cavity, is provided in an area adjacent to the housing opening and is configured to discharge an airflow into the cavity at a velocity of at least 15 m/s.

12. The hand dryer according to claim 11, wherein the at least one lamp is arranged within a strip-shaped area which is located opposite one of the at least one flat nozzle on a sidewall delimiting the cavity and which has edges that correspond to section lines with which boundaries of an angular range ($\alpha$) of ±45°, based on a direction (R) of the air exiting the flat nozzle, intersect the sidewall.

13. The hand dryer according to claim 1, wherein at least areas of at least a part of walls delimiting the cavity are provided with a photocatalyst.

14. The hand dryer according to claim 13, wherein the photocatalyst comprises titanium dioxide, which is contained in a coating applied to a surface of the walls or incorporated into a wall material.

* * * * *